US008898809B2

(12) United States Patent
Müller et al.

(10) Patent No.: US 8,898,809 B2
(45) Date of Patent: Nov. 25, 2014

(54) METHOD AND APPARATUS FOR THE COMBINED ANALYSIS OF A SAMPLE WITH OBJECTS TO BE ANALYZED

(75) Inventors: Torsten Müller, Berlin (DE); Kathryn Anne Poole, Berlin (DE); Detlef Knebel, Berlin (DE); Torsten Jähnke, Berlin (DE)

(73) Assignee: JPK Instruments AG, Berlin (DE)

( * ) Notice: Subject to any disclaimer, the term of this patent is extended or adjusted under 35 U.S.C. 154(b) by 281 days.

(21) Appl. No.: 12/670,570

(22) PCT Filed: Jul. 24, 2008

(86) PCT No.: PCT/DE2008/001203
§ 371 (c)(1),
(2), (4) Date: Jun. 21, 2010

(87) PCT Pub. No.: WO2009/012766
PCT Pub. Date: Jan. 29, 2009

(65) Prior Publication Data
US 2010/0263098 A1    Oct. 14, 2010

(30) Foreign Application Priority Data
Jul. 24, 2007    (DE) .......................... 10 2007 034 854

(51) Int. Cl.
*G01Q 60/00*    (2010.01)
*G01Q 30/04*    (2010.01)
*G01Q 30/02*    (2010.01)
*G01Q 60/42*    (2010.01)
*B82Y 35/00*    (2011.01)
*G01N 21/64*    (2006.01)

(52) U.S. Cl.
CPC ................ *G01Q 60/42* (2013.01); *G01Q 30/04* (2013.01); *B82Y 35/00* (2013.01); *G01Q 30/02* (2013.01); *G01N 2021/6482* (2013.01); *G01N 21/6458* (2013.01)
USPC ..................................... 850/33; 850/1; 850/6

(58) Field of Classification Search
USPC ............................................................ 850/33
See application file for complete search history.

(56) References Cited

U.S. PATENT DOCUMENTS 5,821,409 A    10/1998    Honma et al.
5,874,668 A    2/1999    Xu et al.
(Continued)

FOREIGN PATENT DOCUMENTS

DE    10200408971 B3    5/2006
DE    102007023435 A1    11/2008
(Continued)

OTHER PUBLICATIONS

R. Pepperkok et al., High-throughput fluorescence microscopy for systems biology, Nature Reviews Mol Cel Bio, vol. 7, Sep. 2006, p. 690-696.
(Continued)

*Primary Examiner* — Phillip A Johnston
(74) *Attorney, Agent, or Firm* — Smith Patent Office

(57) ABSTRACT

The invention relates to a method for the combined analysis of a sample with objects to be analyzed, in particular a sample with biological objects, in which measurement results for one or more of the objects to be analyzed in the sample are obtained by analyzing the one or more objects to be analyzed by an imaging method of measurement, probe-microscopic measurement results are obtained for the one or more objects to be analyzed by analyzing the one or more objects to be analyzed by a probe-microscopic method of measurement, and the measurement results and the probe-microscopic measurement results are assigned to one another, after optional prior intermediate processing. Furthermore, the invention relates to an apparatus for carrying out combined analysis of a sample with objects to be investigated, in particular a sample with biological objects.

8 Claims, 7 Drawing Sheets

(56) References Cited

U.S. PATENT DOCUMENTS

Figure 1:
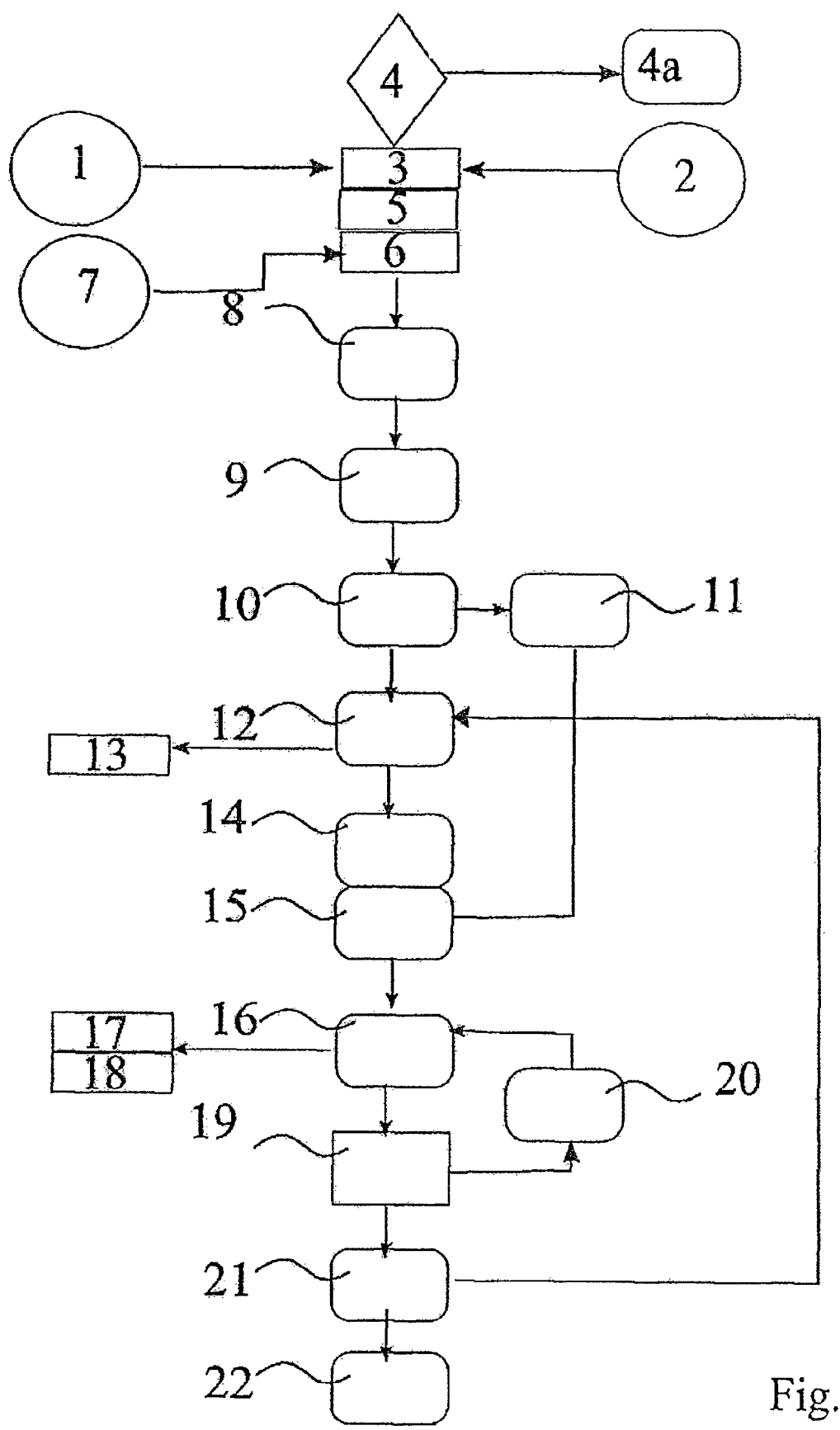

| | | |
|---|---|---|
| 6,858,436 B2 * | 2/2005 | Zenhausern et al. ............ 436/164 |
| 6,862,921 B2 * | 3/2005 | Chand et al. ..................... 73/105 |
| 2002/0048610 A1 * | 4/2002 | Cima et al. ..................... 424/725 |
| 2006/0113469 A1 * | 6/2006 | Baba et al. ..................... 250/310 |
| 2008/0072665 A1 | 3/2008 | Struckmeier et al. |

FOREIGN PATENT DOCUMENTS

| | | |
|---|---|---|
| EP | 0701102 A1 | 3/1996 |
| WO | 2006040025 A1 | 4/2006 |

OTHER PUBLICATIONS

S. Terstegge et al., Hamilton's new cellhost system for full automation of embryonic stem cell cultures, Nature Methods, vol. 1 No. 3, Dec. 2004, p. 271-272.

E. P. Wojcikiewicz et al., Force and Compliance Measurements on Living Cells Using Atomic Force Microscopy (AFM), Biological Procedures Online, vol. 6 No. 1, Jan. 15, 2004, 1-9.

F. Krohs et al., Automated cell characterization by a nanohandling robot station, Division of Microrobotics and Control Engineering, 2007, University of Oldenburg, Oldenburg, Germany, 6 pages.

M. G. Langer et al., A scanning force microscope for simultaneous force and patch-clamp measurements on living cell tissues, Rev. Sci. Instrum., vol. 68, No. 6, Jun. 1997, p. 2583-2590.

A. Taubenberger et al., Revealing Early Steps of $\alpha 2\beta 1$ Integrin-mediated Adhesion to Collagen Type I by Using Single-Cell Force Spectroscopy, Molecular Biology of the Cell, vol. 18, May 2007, The American Society for Cell Biology, p. 1634-1644.

T. Fujii et al., Development of a new force microscope with a fluorescence optical microscope, Thin Solid Films, Elsevier Sequoia S.A. Lausanne, CH, vol. 243, 1994, p. 407-410.

International Search Report, directed to PCT/DE2008/001203, mailed on Oct. 31, 2008, 3 pages.

* cited by examiner

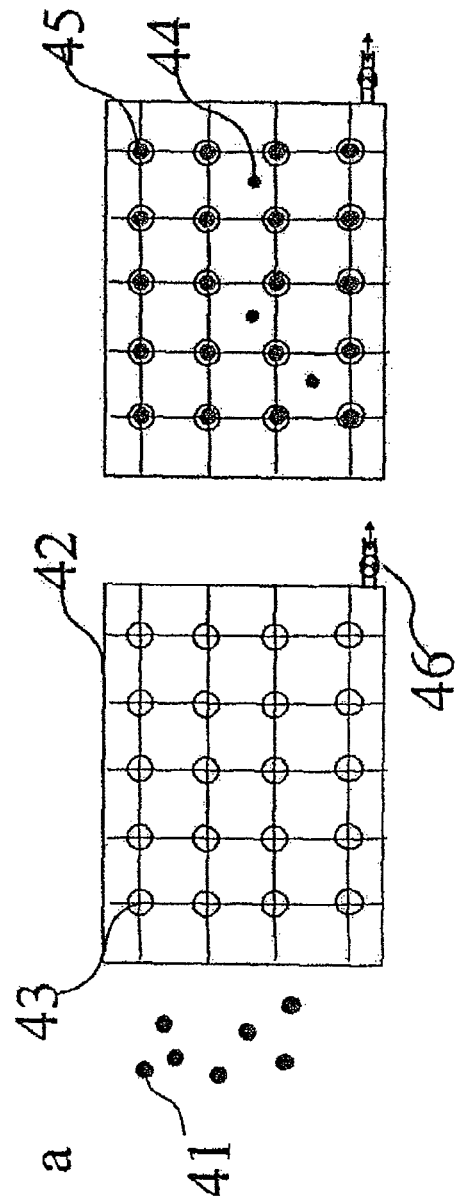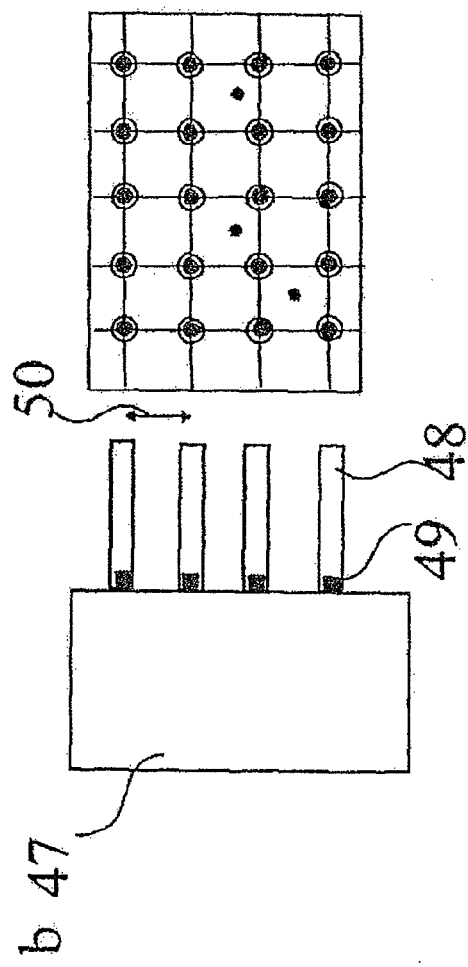
Fig. 3a
Fig. 3b

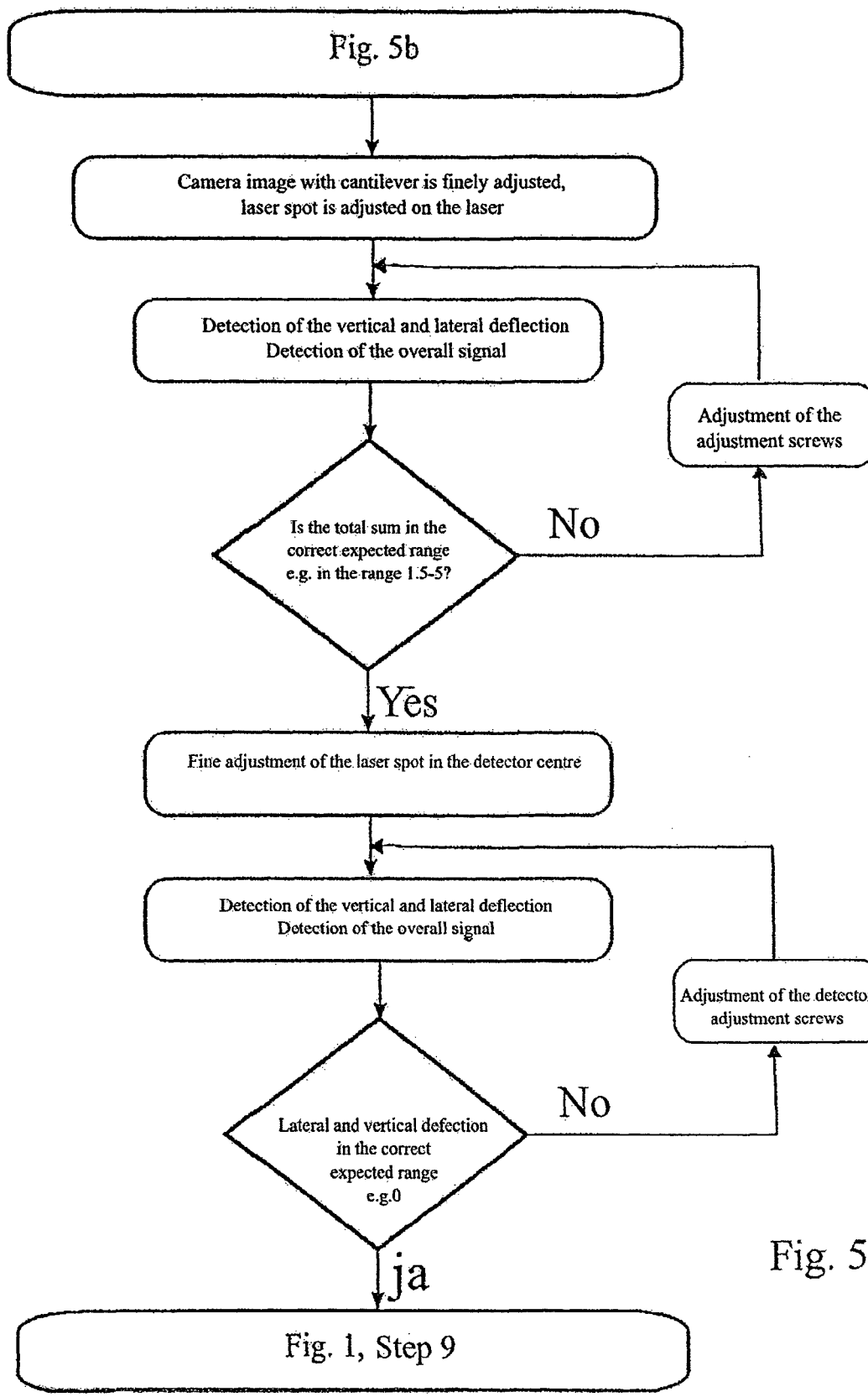

METHOD AND APPARATUS FOR THE COMBINED ANALYSIS OF A SAMPLE WITH OBJECTS TO BE ANALYZED

The invention relates to a method and an apparatus for the combined analysis of a sample with objects to be analysed, in particular a sample with biological objects.

BACKGROUND OF THE INVENTION

Cell biology and biomedical and pharmacological/biotechnological research and production that are dependent thereon are increasing in importance. This is embedded in research into gene and protein characterization, influenced by the Human Genome Project. This now also includes the creation and analysis of siRNA libraries (cf. for example Pepperkok et al., Nat Rev Mol Cell Biol 2006; 7: 690-696, *High-Throughput Fluorescence Microscopy for Systems Biology*) connected with methods for high throughput with automated imaging, optical methods and dispensing.

Several, already existing modules can be defined for this automated image-based high throughput for cell evaluation. To date, a core element of high throughput is automated micrography. This also includes image analysis with the corresponding data management (cf. for example the product Opera from the company Evotec Technologies). Another module can comprise various aspects of fluidic manipulation. This means for example the addition/dispensing of further agents, changing of media etc. For working with cells, the manipulation of cell culture vessels, so-called multi-plates such as 96-well and 384-well plates is essential. This means automated plate changing. In order to keep the cells as viable as possible even for longer-lasting analysis of quite large quantities of plates, various designs of a climate-control module are also offered by commercial suppliers. Meanwhile, some suppliers have developed automated systems, in particular for cultivating adherent animal cells and evaluating them by microscopy. The highly complex systems will not be explained in detail here, as they are commercially available (see for example Terstegge et al., Nature Methods 1, 271-272, 2004, *Hamilton's new cellhost system for full automation of embryonic stem cell cultures*). As a result of analysis, optical (mainly image-based) properties of the biological sample are used in particular for assessment, and features such as pH changes and ion-selective change of the medium only to a small extent.

A technique originally designed for the analysis of individual cells is the classical patch-clamp technique. For the screening of active substances, later on automatic systems were developed, which automate measurement and rinsing procedures and in addition are operated in parallel in a modified planar structure (cf. for example the description of the MDC PatchXpress 7000A, 16-Channel Automated Patch Clamp System, http://www.chantest.com/fastpatch.html). Manual patching is the gold standard—with sensible protocols there are hardly any false-negatives and false-positives. With planar patching, the sensitivity is reduced and the deviation can be at a factor of three, and even more with increased automation, and additionally false-negative results in particular may be increased. Therefore, in the search for active substances, various patch techniques—varying in price, throughput, and accuracy of the information obtained—are employed in the preliminary, main, and final phases of measurement campaigns.

Automated systems and automated imaging techniques for investigating cell-biology processes are known, and are used in the pharmacological, medical and cell-biology research and analysis of active substances including substance screening. Typically, fluorescence-optical properties are evaluated, such as change in intensity of fluorescence, distribution of fluorescence or a shift of fluorescence, which can for example result from energy transport (FRET: fluorescence resonance energy transfer). Measured values are recorded both by confocal and non-confocal techniques. Camera-based image recording is very quick. Depending on fluorescence labelling, camera sensitivity, the objective lens, the resolution and the excitation intensity, typically about 2 to about 100 cells with a cell size of about 10×10 $\mu m^2$ and a cell height of 5 µm are recorded simultaneously at an exposure of for example 40 ms. This speed generally also allows recording of images in different z-heights (z-stack). In optical imaging techniques, image evaluation is the time-limiting factor.

In addition to optical imaging techniques, there are also methods of measurement using scanning probe microscopy (SPM). Scanning probe microscopy is a technique in which a measuring probe scans a sample to be analysed and for example records the topography of the sample. In this connection there is relative motion between the measuring probe and the sample, which is achieved by moving at least the measuring probe or at least the sample. Usually the relative motion is performed as a lateral movement. Additionally, there can also be relative motion in the vertical direction. One form of scanning probe microscopy is scanning force microscopy (SFM). In a scanning force microscope used for this, the measuring probe is designed as a cantilever, which carries a fine measuring tip. The SFM techniques include the AFM technique (AFM: atomic force microscopy).

An SPM measurement can be carried out as a slow, label-free imaging technique. On a cantilever measuring beam there is a suitable measuring tip, for example a ligand-coated particle. The measuring beam and the measuring tip form a measuring probe, which is also called a cantilever. For measurement, a relative motion is performed between the measuring probe and a sample to be analysed, which can for example be cells with a set of receptors corresponding to the ligand. Molecular interactions between the sample (receptors) and the measuring tip (ligand) can lead to a deflection of the measuring probe, which can be documented in particular as bending of the measuring beam.

The SPM technique finds application both in the analysis of molecular interactions between isolated proteins and in the analysis of for example receptor-ligand interactions on cell-cell, cell-particle or cell-substrate samples. The result of the analysis typically comprises a description of mechanical characteristics such as viscoelasticity, strength of adhesion and surface topology. Automation of the SPM technique has been considered, as disclosed for example in documents DE 10 2004 048971 and WO 2006/040025. These describe an automated set-up for measurement and evaluation by scanning microscopy.

If, during probe-microscopic analysis of a sample, there is lateral movement of the measuring probe relative to the sample, a surface image can be recorded with the corresponding mechanical-elastic properties of the sample. A disadvantage is that for imaging when using an AFM microscope, depending on the local resolution of measurement, about 10 min to 1 h is required for one cell. Therefore there are clear limitations on the use of the AFM technique for the industrial screening of active substances. To improve the time factor, the use of multi-cantilevers has been proposed (cf. DE 10 2007 023 435). Alternatively, the areal imaging property of the AFM technique is abandoned and the sample is only scanned at points, so that measurements of local interaction are carried out. This measurement principle is usually known as single cell force spectroscopy (SCFS). The mechanical properties that can be determined by AFM include for example elasticity, e.g. the elasticity of one cell, and measurement of the forces on cell-cell or cell-substrate contacts. With a suitable choice of measuring probe design, the sample can also be analysed electrically.

There are essential differences between the measurement of mechanical properties such as protein-protein interactions and measurements on cell-free preparations and cellular samples. These include the far larger height dimension of cells (z-height) and the discontinuous distribution of the cells. Typically, the cells do not form a uniform continuum on a cultivation substrate in vitro. Their height profile itself and the relative position of important cell organelles can vary, so too can the cell-cell distance and the cell shape. Therefore it is also important in single-cell force microscopy to employ special placement of the measuring tip. A property of confocal microscopy is that only an image segment limited in height to about 1 to 2 µm is obtained. With a larger height dimension of the object to be analysed, in certain circumstances it is important to record several camera images from different heights and evaluate them individually or combine them as a so-called z-stack for 3D illustration.

Furthermore, not every measurement of interaction in single-cell force microscopy is successful. This is strongly dependent on the initial biological situation. Thus, an adhesion frequency of <30% in force measurements (LFA-1/ICAM-1 on A39 cells) has been reported (Wojcikiewicz et al., Biol. Proced. Online 2004:6 1-9, Force and compliance measurements on living cells using atomic force microscopy). This effect can greatly increase the measurement time and the number of cells required. At the same time, however, single-cell force microscopy (SCFS) makes it possible, in contrast to bulk adhesion assays, to resolve various subpopulations and to observe the effect of active substances, for example inhibitors, at the level of the individual cell and even the individual molecule.

It should be noted that optical detection of cells at higher resolution, for example by means of fluorescence, typically requires thin glass, with a thickness of about 170 µm, as substrate. It is important to ensure that the reduced mechanical stability of the thin glass does not lead to vibrations, which can disturb the AFM measurement.

SUMMARY OF THE INVENTION

The problem to be solved by the invention is to create a method and an apparatus for combined analysis of a sample with objects to be analysed, in particular a sample with biological objects, with which the sample can be analysed more efficiently and more accurately. In particular, analyses should also be made more time-efficient.

This problem is solved with a method for the combined analysis of a sample with objects to be analysed according to independent claim 1 and an apparatus for carrying out combined analysis of a sample with objects to be analysed according to independent claim 8. Advantageous embodiments of the invention are the object of dependent subclaims.

According to one aspect of the invention, a method for the combined analysis of a sample with objects to be analysed is created, in particular a sample with biological objects, in which: measurement results are obtained for one or more of the objects to be analysed in the sample, by investigating the one or more objects to be analysed by an imaging method of measurement, probe-microscopic measurement results are recorded for the one or more objects to be analysed, by investigating the one or more objects to be analysed by a probe-microscopic method of measurement, and the measurement results and the probe-microscopic measurement results, after optional prior intermediate processing, are assigned to one another.

According to another aspect of the invention, an apparatus is created for carrying out combined analysis of a sample with objects to be analysed, in particular a sample with biological objects, with an imaging measuring device, which is configured for recording measurement results for one or more of the objects to be analysed in the sample, wherein the one or more objects to be analysed are analysed by an imaging method of measurement, a probe-microscopic measuring device, which is configured for recording probe-microscopic measurement results for the one or more objects to be analysed, in which the one or more objects to be analysed are analysed by a probe-microscopic method of measurement, and an evaluating device, which is coupled to the measuring device and to the probe-microscopic measuring device and is configured for assigning the measurement results and the probe-microscopic measurement results to one another, after optional prior intermediate processing. According to the invention, measurement results from an imaging method of measurement on the one hand and probe-microscopic measurement results from a probe-microscopic method of measurement for the same sample are combined with one another, so that both the possibilities for evaluation of the measurement results and the accuracy of analysis of the sample are improved. The measurement results of the different methods of analysis are assigned to one another, so that measurement results from the imaging method of measurement are related to corresponding probe-microscopic measurement results and vice versa. It can optionally be envisaged for the measurement results obtained in the respective methods of measurement to be processed first, before being assigned, for example to optimize a signal-noise ratio or for smoothing. In this way, the assignment of the measurement results from the different methods of measurement is possibly also facilitated.

The imaging method of measurement is preferably an optical imaging method, in which for example an image is produced using an image recording device, e.g. a camera device. In one embodiment the image recording device can be combined with a light microscope.

A preferred further development of the invention envisages the imaging method of measurement and the probe-microscopic method of measurement being automated and carried out as combined measurement of the sample. The imaging method of measurement and the probe-microscopic method of measurement can be carried out in parallel in time, at least partially.

In a preferred embodiment of the invention it can be envisaged that information on the properties of the sample is derived from the measurement results and is taken into account when carrying out the probe-microscopic method of measurement.

An advantageous embodiment of the invention envisages that positional information on the position of the one or more objects to be analysed in the sample is derived, as information on sample properties, from the measurement results and is taken into account for positioning a measuring probe, used in the probe-microscopic method of measurement, relative to the sample.

A preferred further development of the invention can envisage that information is derived from the probe-microscopic measurement results, which is taken into account when carrying out the imaging method of measurement. If for example the probe-microscopic method of measurement is carried out by recording a force-distance curve, the acquisition of measurement results for the imaging method of measurement can partially be triggered by acquisition of measured values for the imaging method of measurement being started when specified values of the curve, in particular defined by the user, are reached in the force-distance curve. For example, in this way the recording of a sample region of interest using an image recording device can be initiated when a threshold or trigger value is reached in the force-distance curve. In this way, measurement results from the two measuring methods, combined together, are assigned to one another. In the image data recorded as a result of triggering, it is possible for example to record in what region of the surface of the sample to be analysed, the measured value of the probe-microscopic analysis initiating image recording was obtained. Assignment is carried out between the measuring probe position relative to the sample being analysed in the image recording and the measured probe-microscopic measured value. Said coupling of the measurement results can also be provided for other types of probe-microscopic analysis, which differ from the recording of a force-distance curve. This includes for example the so-called force clamp mode, in which for a selected time the contact force on the object is kept constant.

As a reaction to the triggering of the imaging method of measurement on reaching a defined measured value in the probe-microscopic analysis, it can furthermore be envisaged for the probe-microscopic method of measurement subsequently to be analysed further with altered observation parameters. For example, in conjunction with scanning of the sample to be analysed by means of the measuring probe of the probe-microscopic measuring device, a new distance setting between sample and measuring probe can be used.

Preferably, a further development of the invention envisages that, in the imaging and the probe-microscopic method of measurement, the sample is arranged in a fluidic cell.

In an advantageous embodiment of the invention, it can be envisaged that, in the imaging and the probe-microscopic method of measurement, cells are analysed as the object to be analysed in the sample.

A further development of the invention can envisage that further probe-microscopic measurement results are recorded for the one or more objects to be analysed, with the one or more objects to be analysed by the probe-microscopic method of measurement being analysed again, using altered observation parameters, which differ from observation parameters of the probe-microscopic method of measurement previously carried out.

A preferred further development of the invention envisages that the imaging method of measurement using at least one measurement technique, selected from the following group of measurement techniques, is carried out: electrical imaging method of measurement such as patch-clamp and impedance measurement, chemical imaging technique such as local pH measurement or ion-selective measurement of values and optical imaging method of measurement.

In a preferred embodiment of the invention, it can be envisaged that the probe-microscopic method of measurement is carried out using at least one measurement technique selected from the following group of measurement techniques: scanning probe microscopy, atomic force microscopy and optical force microscopy.

The foregoing, advantageous embodiments of the method for the combined analysis of a sample apply correspondingly to possible further developments of the apparatus for carrying out combined analysis of a sample. The apparatus can then be implemented according to the respective embodiment of the method.

With the techniques proposed according to the invention for the combined analysis of a sample with objects to be analysed, probe-microscopic and microscopic imaging analysis can be automated.

The combination of the methods of measurement can be used both for the characterization of mechanical-physical and biochemical properties and for the morphological/physiological characterization of biological samples, in particular of living cells. The accuracy and depth of the information provided by the analysis are thus improved. The experiment is speeded up, and the costs relating to personnel and training can be lowered. Especially in the area of cell-cell, cell-particle and cell-substrate analyses, the method is increasing in importance. Fields of application include immunology (analysis of B-cell receptors), cancer research (metastasis, immunology, developmental biology and the biology of infection for the elucidation of molecular and cellular mechanisms of action and for finding active substances in cellular-based screening in the pharmaceutical-biotechnological industry.

The probe-microscopic measurement is preferably carried out using a form of scanning probe microscopy. The scanning probe-microscopic methods of analysis include for example AFM measurement. Said measurement comprises an embodiment essentially consisting of the following steps A) to G). For a better understanding, the defining sections will be briefly explained. Individual deviations should not, however, affect the general concept.

A) Preparation of samples and substrates
Functionalization of the AFM probe, for example with Concavalin A (biotin-streptavidin-biotin/ConA)—This is carried out typically about 24 h before the experiment for several tips simultaneously and is not time-critical for the actual measurement. Functionalization with ConA produces very strong binding to a cell or a particle, which have a large number of corresponding membrane-bound sugars.

Cell- or protein-immobilization on a substrate: The sample substrate does not have to be restricted just to cells or proteins, but can also relate to polymers such as polylysine, sugars, amino acids and other components used in connection with problems in cell biology. The preparation time depends on the actual coverage, and typically cells and proteins are applied to a substrate 1 to 24 h beforehand.

B) Commissioning of the complete equipment, which in one embodiment has at least one imaging system, preferably a microscope, a probe-microscopic system, a fluidic system and a data processing unit.

C) Installation of the cantilever

D) Calibration of the cantilever

E) Steps for carrying out the actual AFM measurement (see also: Taubenberger et al., Revealing early steps of $\alpha_2 \beta_1$ Integrin-mediated adhesion to collagen type I by using single cell force spectroscopy Molecular Biology Cell 18, 1634-1644, 2007):

charging of the measuring probe. This can comprise cells, particles or just the treated or untreated cantilever itself (time T=Tloading). This is a very variable step. Referring to an account by E. P. Wojcikiewicz et al. Biol. Proced. Online 2004:6 1-9, they are applied to the sample carrier with the target substrate and, in a manual version, are brought from there onto the AFM tip: (i) washing-in of the probe cells, this can take place in the immediate vicinity of the target cells or in a separate target-free region of the measurement space, (ii) focusing of the camera (objective) on the cell, moving the cantilever closer to the cell, careful contacting for a short time of about 1 to 5 s and an adhesion time of about 1 to 5 min, to ensure definite, firm contact of the particle-based probe with the cantilever, (iii) optionally washing-away of the surplus probe cells, and (iv) positioning of the probe near the target substrate bringing the measuring probe closer to the target substrate (T=Tapproach)

contact between probe and substrate=Tcontact about 50 ms to 1 s (or 5 to 600 s)

retraction Tretract separation Tseparation. The separation can comprise several 10 micrometers, depending on the viscoelastic properties especially of the target substrate.

recovery time, to give the probe cell a recovery phase (2 to 3 min), this can refer to the target cell, if this is to be sampled repeatedly addition of an active substance and subsequent time of action repeating the experiment 2 to 5 typically 2 to 20× per cell and for 10 to 20 cells: with usual 20 to 80 force curves altogether, about 20 sec/cell with about 20 to 30 min for a complete experiment, when the same probe can be used, rinsing and possible addition of further agents or charging with new measuring probe or replacement of the cantilever at point C)

F) Cleaning

G) Evaluation of the data

The proposed method with imaging measurement and probe-microscopic measurement, in particular scanning probe-microscopic measurement, can be carried out, in a preferred embodiment, as follows: automated cantilever adjustment, determination of the position of the biological sample on a carrier and the probe position, subsequent alignment between sample and measuring probe, time coordination of all relevant systems such as image-optical technology, with probe microscopy and sample holding and fluidics, and dispensing and other handling systems, adjustment of automated selection and position determination of several objects of the sample with subsequent recording (multiplexing) of at least one first optical property of the sample and automated recording of at least one first mechanical property of the biological cell sample by SPM and correlation of the mechanical and optical property. In a further step, intermediate evaluation can be followed by further optical and mechanical sampling.

Automation in conjunction with AFM measurement for living cells can be divided into three main applications: (i) cell-cell, cell-particle or cell/particle—substrate interaction measurements for the characterization of molecular interactions by force spectroscopy, (ii) measurements of cantilever-cell interactions and (iii) measurement of cell stiffness. All three applications can moreover be connected with fluidic support and can comprise rinsing procedures and addition of active substance. Furthermore, it can be envisaged that the probe holder not only contains a cantilever, but is equipped with a multi-cantilever. It can then be envisaged that an unusable cantilever is removed and is stored in a separate region. For clarity, the improved design will be explained in more detail on the basis of application (iii).

The proposed method and the proposed apparatus can be used for automation of the analysis, which leads to considerable advantages in the serial and parallel processing of processes and data. The recognition and selection of suitable target cells takes place by automated image-object recognition and recording of a 1st image (data set) at time T=0. For example, in a first step with a smaller objective, which offers a larger image section, the approximate position of sample cells is determined, then in a second step it switches to a larger objective and the position of the individual sample cells is determined, at greater binning of the camera. Then in the third step, the camera (exposure time, binning) and/or illumination parameters (intensity) and the z-focus are adjusted to an optimum first image recording for assessment of the sample in question. In a fourth step, a first analysis of state of the cell is evaluated and the x,y position for a sampling is calculated. This determination of the position and of the initial state is carried out for several cells. If a cell that is examined proves to be unsuitable in the first optical evaluation, the process begins with a new cell. If there are no, or insufficient, cells in the camera image section examined, the sample can be moved in the x,y plane.

It can be envisaged that after a first force measurement the cell requires a recovery time. It is therefore proposed to sample the previously determined target cells in this time segment one after another (multiplexing). Ideally the recovery time in the minute range is greater than the time that is required for a force measurement and optical image recording on several individual cells. A considerable saving of time can thus be achieved. In addition, the experimental stress of the cells can be reduced.

It can further be envisaged that after a first sampling of several individual target cells, these are loaded with an active substance. After a necessary incubation time and a rinsing process, the cells originally analysed beforehand are approached again in the corresponding order and sampled. In this way the dispersion of the measured values is reduced by measuring individual cells.

It can also be envisaged that optical image recording is coupled with passing through characteristic points of the force-distance curve. When passing through a schematically represented force-distance curve (cf. FIG. 2 below), characteristic points occur. The recording of optical images in position (cf. reference symbols 30 and 36 in FIG. 2) is very simple and can also be carried out manually. In an automated and time-coordinated analysis it is possible both to agree a particular optical image sequence beforehand (also while varying the z-focus by moving the objective—z-stack) at selected characteristic points, wherein the actual force-distance values can vary individually from sample to sample, and to couple the image sequence with the attainment of uniform established distances and/or forces. The attainment of the characteristic points itself emits a signal for a trigger to start optical image recording.

It can be envisaged that both from the imaging measurement and from the probe-microscopic measurement, a decision tree is passed through, i.e. a decision is taken regarding the optional progress of the analysis depending on the measurement result. If, after running through a first analysis, for example an expected value of the SPM measurement, for example the number of breaks, is not reached, the SPM measurement is repeated with altered parameters, for example force, contact time or speed. Alternatively it can be envisaged that after the SPM measurement and the optical images, a data evaluation shows that for example an expected value from the optical image data was not fulfilled. This generally means image data, such as are employed for the optical characterization of microparticles and cells, for example intensity, intensity distribution and/or intensity conditions with different fluorescences. Then the SPM measurement takes place once again. During this, one parameter is altered, for example the tracking force or the contact time. Then, from an immediate image evaluation, it is possible to determine which SPM parameters produced which effect on the sample. This type of measurement can be applied advantageously for example during combined analysis of the cell response to mechanical stimulation.

Time coordination of the movement of the cantilever, supporting systems such as dispensing, of the sample holder, of the microscope and of objectives on the one hand and the optical image recording (for example with a camera) on the other hand is an important aspect in one embodiment. It permits satisfactory assignment of optical recording, SPM measurement, addition of active substance and physiological action.

It can further be envisaged that as a result of an automated measuring operation, subsequent parameters are recorded. For this, not all features have necessarily always to be recorded and issued: repeat rate of the individual measurements; concentration series connected with recording LD 50; positive control; negative control (for example buffer); testing whether the action of a substance can be reversed by rinsing with a rinsing buffer; test conditions—for example incubation time, incubation temperature; carrying out measurements of several cells; with several active substances (compounds); and information on the local spatial distribution of cells with their individual properties for the detection of subpopulations and more uniform cell clusters.

It can also be envisaged that a sampling, for example for taking up cells, has an array-like substructuring. As a result, an otherwise rather random distribution of the cells from the sample or of particles for the measuring probe is removed and transferred to a special storage zone. In this way locating the objects and automatic sampling are facilitated. For example, the sampling can have a row-and-column arrangement of pores with a diameter smaller than the dimension of the individual sample. By applying a vacuum, the suspended objects are sucked onto the pores and retained, as is known from the planar patch-clamp technique. Objects outside of the pores can be flushed away by a cross-flow. The positioning can also be effected by overpressure. Pumps are typically used for generating the pressure.

The array-like positioning of the objects can alternatively also be effected by micro-spotting of the objects with a dispenser. This method is especially attractive when the topographical recording is populated with an array-like matrix of substances that promote (for example polylysine, fibronectin) or inhibit (for example polyHEMA) the adding-on of microobjects, in particular cells. Such a matrix is produced as standard by spotting or contact printing (for example nano- or microimprinting). Another form of array arrangement can also be produced by geometric solid shapes, as shown by NUNC with the LiveCellArray (www.nuncbrand.com).

Following SPM measurement, it is proposed to cultivate the samples further for additional measurements. For assignment of later data for individual objects in the micrometer range to be possible, at least one position labelling, for example a 2-point labelling, must be present on the substrate.

Furthermore, it can be envisaged that for automated measurement of living biological samples, the measuring chambers must also be adapted to the requirements. In addition to control of temperature and $CO_2$, control and regulation of air humidity is also necessary. For this, a climate-control box around the SPM measurement and observation unit is proposed, which is simultaneously vibration-damping. A circulating process is useful for uniform temperature and gas distribution. So that no vibrations occur during the SPM measurement, if necessary the vibration-inducing control system is switched off during the actual measurement.

Furthermore, provision of a fluid inlet/outlet on the measuring chamber can be envisaged. A fluid connection that is spatially and mechanically independent thereof and comes from the direction of the cantilever holder can also be provided. This can be achieved with a feed line fitting into the holder or with a dispensing or micropipetting unit fitted mechanically independently of the cantilever holder. This second feed permits, especially with separately mounted measuring chambers, rapid, volume-reduced supply with active substances for the measurement.

It can be envisaged that the aforesaid properties of the measurement space apply not only to a solitary measuring chamber, but also in the case of a collection of chambers. In one embodiment it is proposed that the partitions of the chambers have flatter partitions than the outside walls. The separate measuring chambers can be filled fluidically separately. If the level exceeds the height of the partitions, the latter are in a so-called fluidic continuum. In this way the measuring probe can also be moved from one measuring chamber to the next, without leading to pronounced mechanical loading, especially of the measuring probe. In one embodiment of these corresponding measuring chambers it is also possible that not all units of the multichamber communicate with one another fluidically. Furthermore, spatial separation of particles for the measuring probe and for the AFM sampling is proposed. The advantage is that previous interaction of both types is prevented and an incubation with an active substance does not necessarily act on both types, and easier optical object recognition for example in the charging phase.

Automatic adjustment of the position of the laser beam on the cantilever and its image on the detector can also be carried out by altering the mirror position (cf. below FIG. 1, step 8). It can be envisaged for the position recognition of the laser to be of image-based design. In this, the brightness distribution is read off by a camera on the objective side, and analysed row-by-row or column-by-column and adjusting buttons are altered by control elements until the distribution found tallies with a range of expected values. In a first object-locating step it is possible to use an objective with lower magnification. Then the system switches automatically to the working magnification and carries out fine adjustment. During adjustment of the mirror, the data already available are used for laser alignment, which is effected by motorized control elements. The resultant values are compared with the existing quality values, optionally the calibration is repeated, recorded and, on request, the user is offered information for optimization and correction of errors. Furthermore, the test procedure can be used for carrying out regular optical control of the intactness of the cantilever, as breaking-off of an arm of the cantilever can change the spring constant considerably and thus dramatically influence the conclusions from the measurements. A special advantage during adjustment could be achieved if the cantilever already has a window of thinner material or a different coating or texture, which increases contrast considerably, so that the image-based adjustment can be carried out all the more reliably.

It can moreover be envisaged that all data relevant to the experiment, for example type of cantilever, spring constant, SPM data such as force, speed, loading rate and images, time control and additions of substances are filed in an unalterable raw data set, which satisfy the requirements of Good Manufacturing Practice (GMP) or Good Laboratory Practice (GLP) for quality assurance in the pharmaceutical/biomedical area.

Furthermore, it can be envisaged that the analysed objects are still in a viable state after the sampling. Especially when there is a nonuniform distribution of objects with special remarkable properties (subpopulations), it is necessary for these to be isolated. A usual chemical separation of all objects of a chamber is ruled out for this. Therefore alternative object isolating techniques are proposed, such as cutting out with a laser ("cut and move"), removal by micropipetting techniques or working with dielectric or magnetic tweezers.

The term fluidics describes not only possible hoses and connectors, but also refers to pumps, valves, injectors, mixers and dispensers, which are required for carrying out the experiment.

In addition to the AFM and SPM techniques, other methods can also be envisaged, with which molecular interactions during particle-particle and particle-substrate interactions (a cell can also be a particle) or viscoelastic properties of the samples can be measured. This includes the PFM technique (PFM: photonic force microscopy) and the laser-tweezer technique and the micropipetting technique. These probe-microscopic methods of analysis can also be combined individually or in any combination with the imaging method of analysis.

DESCRIPTION OF PREFERRED EXAMPLES OF THE INVENTION

Figure 2:
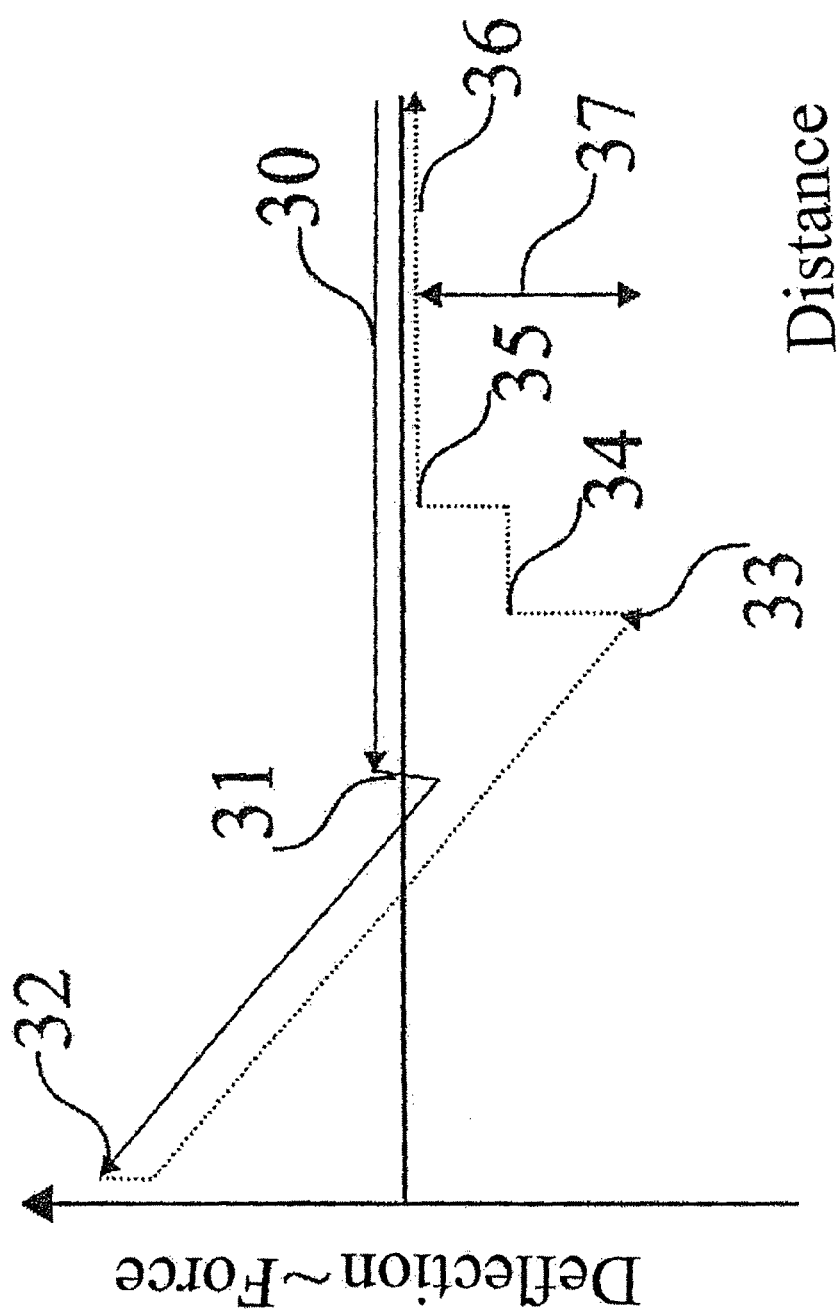
Figure 4:
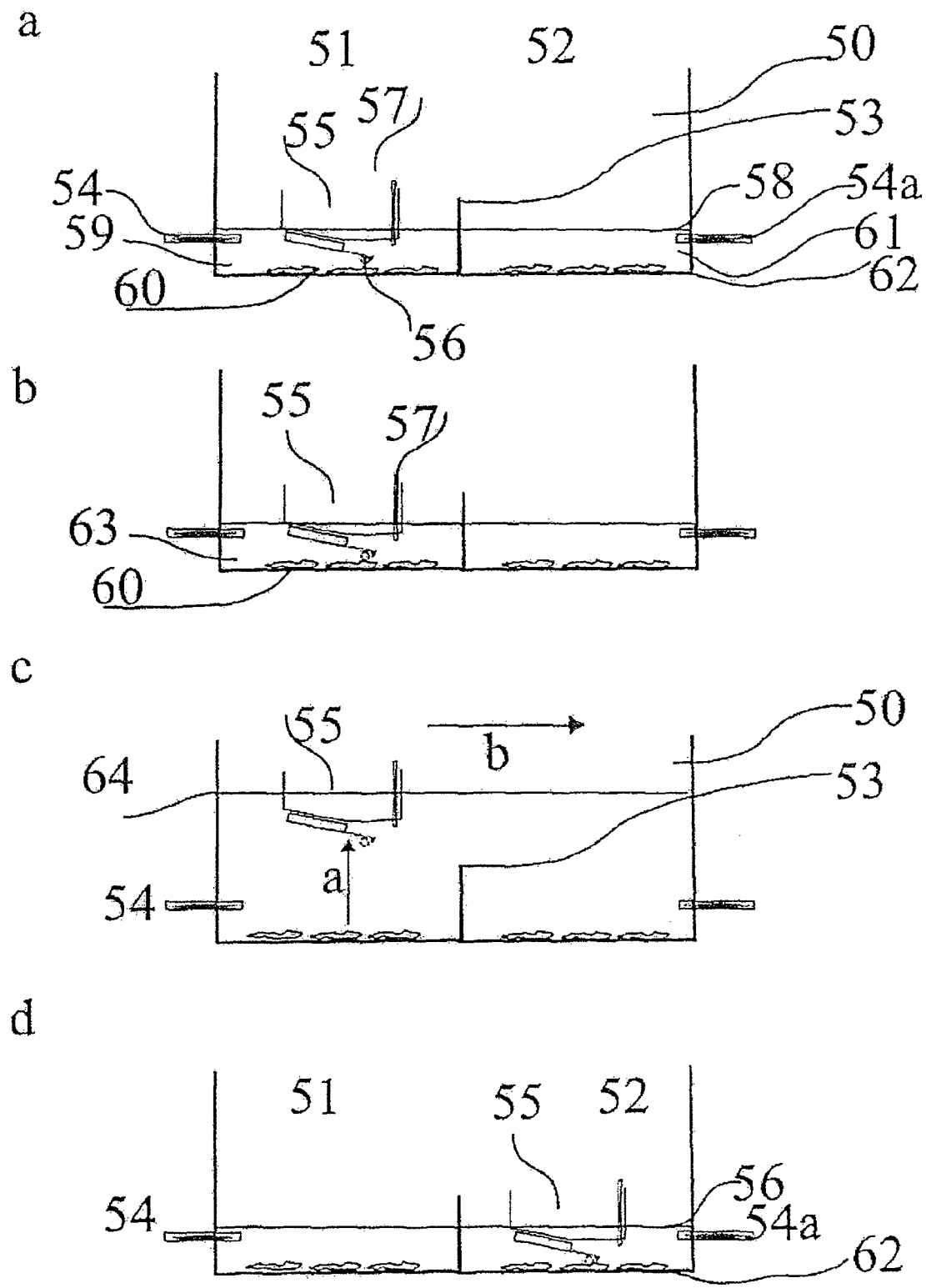
Figure 5A:
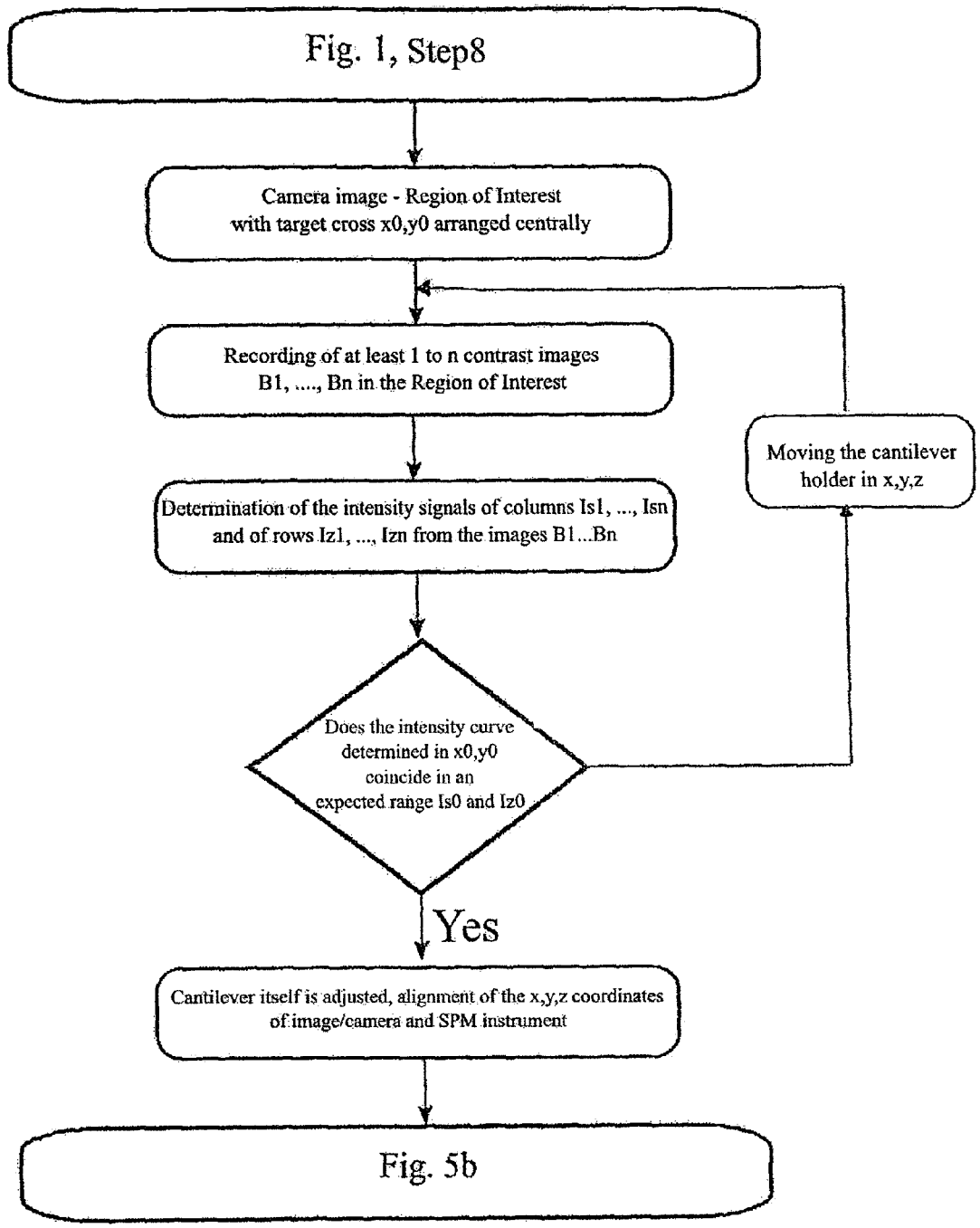
Figure 5B:
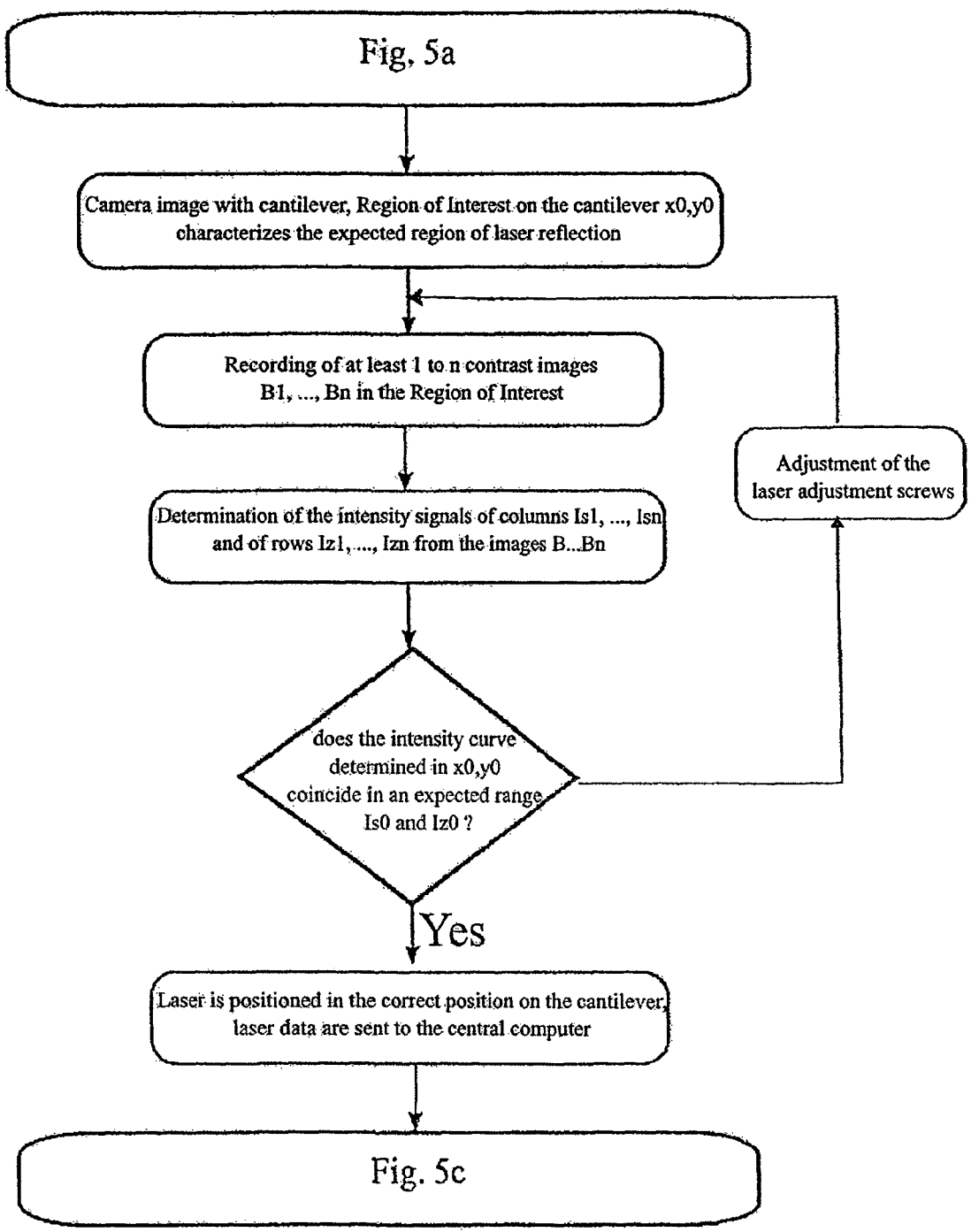

The invention is explained in more detail below on the basis of examples, referring to diagrams in the drawings, showing:

FIG. 1 a flow chart for a method for the combined analysis of a sample using an imaging method of measurement and a scanning probe-microscopic method of measurement, FIG. 2 a schematic illustration of a force-distance curve with characteristic measuring points, FIG. 3a a schematic illustration for an arrangement of measuring chambers with different compartments for a sample, a measuring probe and a measuring probe storage zone, in a top view, FIG. 3b a schematic illustration of an arrangement with a multi-cantilever and an array formation with corresponding geometry, FIGS. 4a to 4d a schematic illustration for describing a measuring probe transfer with scheduled fluid replacement and FIGS. 5a to 5c flow charts for describing a control circuit for an automated adjustment of a measuring apparatus.

FIG. 1 shows a flow chart for a method for the combined analysis of a sample using an imaging method of measurement and a scanning probe-microscopic method of measurement.

Preparation of the samples (step 1) and of the measuring probe(s) (step 2), which can also include a first functionalization, is carried out separately. The measuring instrument 3 with a data processing and analysis unit 4 additionally optionally connected to a separate unit for the data evaluation/storage step (4a) are put in operation. Following a reference run (homing process) of the x,y,z axes of the sample carrier unit (step 5), it takes up a working position. Then the measuring probe/cantilever (step 2) and the sample are mounted in the measuring instrument 3. The measuring probe, sample and its specific holder form a separate sample space 6, which is equipped with a fluidic system (step 7). The sample space 6 is filled in step 4 by means of the fluidic device 7.

In step 8, automatic adjustment of the position of the laser beam on the cantilever and of its image on the detector is achieved by changing the mirror position, for example via electromechanical control elements. In a process presented in more detail in FIGS. 5a to 5c, the x,y,z position of the cantilever is determined, supported by a reference run and object recognition.

In another step 9, calibration of the cantilever 2 is carried out. In the next step 10, the spatial position of the cantilever and of the sample substrate is determined and they are synchronized with one another. An essential aspect is that there is not only alignment of spatial coordinates, but also time-based synchronization of all relevant elements, in particular image recording of the camera and detection of the movement of the cantilever and movement of the cantilever holder itself. Positional determination of cantilever sample substrate can also be carried out alternatively on a target sample or a probe sample (particle for the measuring probe). During this, fine adjustment of the x,y,z position of the target sample takes place. Using the autofocusing procedure in particular, the optical interface for transparent carriers is determined reliably. Next, the sample position is aligned with the cantilever position. Allowance is also made for the fact that the optimum position of a cantilever carrying a probe is different from one without a probe.

For the actual force measurement, the measuring probe is moved to a waiting position (step 11). Next, suitable target cells are selected by automated image-object recognition (step 12) and recording of a 1st image (data set) (step 13). Furthermore, x,y coordinates are found from the image (step 14) for positioning the measuring probe (position from step 11) and this is moved to the respective position obtained. Image recognition can take place by a method similar to that described in FIG. 5a or on the basis of algorithms for object and cell recognition that have been entered. This can be achieved both by the standard transmission set-up and contrast method, and with fluorescence microscopy. The recognition itself can take place in two stages: (i) recognition of potential target cells by a coarse intensity analysis—in this case the x,y,z positions of these objects have already been filed. If there are no objects in the field of view, after reporting back to the process unit, the sample carrier is moved in the x,y direction, and (ii) an image-based characterization and selection of the target cells is connected.

After bringing the measuring probe closer to the sample—target cell (step 15), the scanning probe-microscopic analysis is carried out in step 16. After the SPM analysis with the results (step 17), a 2nd image (data set) 18 is recorded.

Depending on the task, the information from the two sets of images can be processed similarly and combined with the force measurement and evaluated.

Via a decision matrix (step 19), the experiment can be repeated with the same or with altered parameters. Recording of a 2nd image data set can also already take place during sampling and, depending on the result, can influence the setting of the AFM parameters immediately. Furthermore, it is possible for the 2nd image data set to be recorded at an altered focus height, as is done when recording a z-stack.

Depending on the assay conditions, it may be necessary to carry out the measurement at staggered intervals. For differentiating subpopulations it may also be advantageous, for each of the individual cells, to alter the variation of setting parameters of force microscopy such as contact time, tracking force, traverse rate and loading rate (step 20) or to change the focus setting. All parameters can also be modulated with respect to time and/or position.

The measured values can now be recorded once again for several individual cells. In the next step 21, the sample is provided with an active substance and the measurement is repeated. Depending on the assay conditions, it may be necessary to carry out the measurement at staggered intervals.

For differentiating subpopulations it may also be advantageous to alter, for each of the individual cells, the variation of the setting parameters of force microscopy such as contact time, pressure, and loading rate.

Then the measuring probe is rinsed and the experiment is stopped (step 22).

FIG. 2 shows a schematic illustration of a force-distance curve with characteristic measuring points.

Here, the deflection of the cantilever is proportional to the force acting vertically on the cantilever or the measuring probe. The distance is the distance between the sample and the cantilever tip—also called the measuring probe. The arrows drawn with solid lines symbolize the approach movement—attraction, whereas the dotted lines describe movement away—retraction of the cantilever from the sample. The cantilever is not a completely rigid beam, but can experience concave or convex deflection when moving to and from the sample, whereas the actual tip/measuring probe is still in contact with the sample.

The measuring point 30 describes the approach of the cantilever tip to the sample from a greater distance away. At the end of the approach, the tip jumps suddenly onto the sample surface (measuring point 31) owing to forces of attraction. Further approach of the cantilever with the probe leads to a further increase in the repulsive forces (cf. measuring point 32), when the tip is in very close contact with the sample surface. In this case measuring point 32 stands for the closest approach between tip and sample. The cantilever then moves away from the closest contact again, whereas the tip is still in contact with the sample (cf. measuring point 33). At the end point, there is maximum deflection of the cantilever. Whereas the cantilever moves only very slightly from the sample and the tip is still in contact with the sample, there is a sudden change in cantilever deflection (cf. measuring points 34, 35). This is for example the case when material is withdrawn from the sample (for example threads—"tether" are pulled from membranes). The deflection of the cantilever is suddenly altered, without any motorized change of the cantilever itself. Overall, there is a sudden decrease in the required tensile force. FIG. 2 also shows the following measuring points: 37—maximum deflecting force at point 33, 36—from end of 35 and start of 36 the tip is no longer in contact with the sample and is moved farther away.

An automated measurement sequence according to an example within the flow chart presented in FIG. 1 is described below, referring to FIG. 2.

A cell to be analysed is stained with a dye, which accumulates in vesicles inside the cell. Based on the pH normally present in the vesicles, the intensity of the dye in a filter region examined is very slight. Observation uses a suitable inverted microscope using a CCD camera. An average pixel intensity is determined from a measurement region of interest, in which the cell is located. If the cell is activated owing to mechanical loading, for example by means of a cantilever, this leads to a change in the pH of the vesicles and thus to an increase in dye intensity. If the cantilever is suitably coated, for example with fibronectin, the strength of interaction with a receptor, for example integrin, can be measured on activated cells from the force-distance measurement (FIG. 2, measuring points 33 to 36).

In the probe-microscopic analysis, the cantilever is positioned over the cell and begins, with preset values, to approach the cell surface (cf. region 30 in FIG. 2) at a speed v1 (constant deflection, in the region of zero). In this phase, a first camera image (first image data set) is recorded with a selected camera setting (for example binning, exposure time), and approach is stopped or slowed down markedly. The intensity is determined within the region of interest and is stored for corresponding cantilever properties such as degree of deflection as a measure of the force and the present z-position. If the intensity found is below a preset expected value (negative control), the approach is continued.

At measuring points 31, 32 there is an increase in the deflection of the cantilever. Within the approach phase, at measuring points 31, 32, further camera images are recorded regularly with camera settings that are the same as or different from the settings used for the first camera recording, and in the meantime the movement of the cantilever is typically stopped or slowed down markedly. Within the region of interest, the intensity is determined continually (within the total time for image recording and evaluation) and is stored for the corresponding cantilever properties and the time.

This process is carried out up to the degree of deflection of the cantilever at which the intensity of the region of interest is for the first time above a given expected value (positive control). Transition to the phase with the measuring points 33, . . . , 36 only takes place after that. This has the advantage that both the activation can be initiated for the cell and documented, and the corresponding force-distance curve can be recorded. As a result, the number of measurements required is reduced.

FIG. 3*a* shows a schematic illustration for an arrangement of measuring chambers with different compartments for a sample, a measuring probe and a measuring probe storage zone, in a top view. FIG. 3*b* shows a schematic illustration of an arrangement with a multi-cantilever and an array formation with corresponding geometry.

In a measuring chamber 42, there are pores 43 a defined distance apart, thus forming an array. The measuring chamber 42 is connected fluidically so that, through a combination of valves and pumps 46, a suction pressure can be induced above the pores. On adding particles 41, the particles are sucked onto unoccupied pore sites. This results in an array-like arrangement of particles 45. Alternatively, placement can also be produced with overpressure. The arrangement can also be cleaned in this way. Furthermore, optionally surplus particles 44 are stored on intermediate areas. These can then be rinsed away, whereas the placed objects 45 remain stable locally. The fluidic contacting is preferably designed so that a row-by-row or column-by-column loading is possible.

FIG. 3*b* shows an AFM measuring probe, which consists of a main body 47 and a cantilever 48 with an additionally fitted piezo-control element 49. Preferably, with a multi-cantilever, the cantilever distance 50 should be the same size as the corresponding array distance. The individual bending beams of the multi-cantilever can also be addressed and read individually.

FIGS. 4*a* to 4*d* show a schematic illustration for describing measuring probe transfer with scheduled fluid replacement and It can be seen from FIG. 4*a* that a measuring chamber 50 is divided into two partial regions 51, 52, which are separated by a partition 53. Each of the partial regions 51, 52 has, in the example shown, a fluid feed 54, 54*a*, which can be operated independently of one another and can both suck and pump. In addition to a cantilever holder 55 with cantilever and measuring probe 56, there is another fluidic feed 57, which can function for example as an integrated micropipette or as a dispensing unit. Both partial regions 51, 52 are filled up to a liquid height 58, and in solution I 59 there are particles 60 and in solution 61 with objects 62, the composition can be the same as solution I 59 or different.

In FIG. 4*b*, first an SPM measurement of the measuring probe is carried out on a particle 60. Following a first measurement, an active substance (solution 63) is washed in via 57 and measurement is repeated. After the SPM measurement, partial region 51 is rinsed again via 54, so that 51 and 52 essentially contain an identical fluid.

In FIG. 4c, the measuring chamber 50 is flooded above the height of partition 53 and up to a liquid level 64 by means of the inlet 54. Accompanying the increase in level, the distance between cantilever holder and particle 60 is increased (arrow a). Then the cantilever is positioned above the second partial region 52 (arrow b).

In FIG. 4d, the liquid level 64 is lowered to the original level 56 over the fluidic port 54 or 54a, accompanied by lowering of the cantilever holder with the measuring probe to a working position in the vicinity of the sample particle. In addition, replacement of the liquid takes place, so that in the two partial regions 51, 52 individual solutions are again present and sampling of the particles 62 is carried out.

FIGS. 5a to 5c show flow charts describing a control circuit for automated adjustment of a measuring apparatus.

FIG. 5a starts after step 8 in FIG. 1. The aim is first to image the cantilever tip itself in the microscope-camera image and carry out alignment. It can be assumed that the position of the cantilever tip is known approximately. Depending on the selected objective, however, the tip can lie outside of the camera's field of view. First a centering cross is indicated centrally in the camera. The aim is to line up the cantilever tip with the centre of the cross. For this, at least one camera image is recorded, recording the intensity signals row-by-row and column-by-column. The appropriate pixel size of the rows or columns must be tested beforehand, but should be in the region of half the cantilever width. The position of the cantilever tip can be determined from the intensity pattern. If the position still does not coincide with the target region, a corresponding correction of alignment is carried out by means of servomotors and the intensity distribution is determined once again. In this way the position in the x,y plane can be matched to the expected value. To achieve the correct focus height of the cantilever, yet another contour analysis is carried out by means of an intensity analysis. For this it may be useful to switch over to another type of illumination (not shown here). In this way it is possible to match the position of the cantilever tip in the x,y,z direction with the camera image.

In FIG. 5b, storage recognition of the detection laser is also carried out based on images. In this case the brightness distribution is read with a camera on the objective side and is analysed row-by-row or column-by-column, as already described in detail in FIG. 5a. The expected intensity patterns are of course different. The control elements perform motorized variation of the adjusting buttons until the distribution determined coincides with an expected value range. In a first object-locating step, an objective with lower magnification can be used, then the system switches automatically to the operational magnification and performs the fine adjustment.

The adjustment of the mirror is described in FIG. 5c. First there is optimization of the laser setting according to the overall signal by means of motorized control elements. In a second step, the vertical and lateral deflections are optimized according to an expected range. The resultant values are compared with the present quality values, and optionally the calibration is repeated, recorded and information on optimization and correction of errors is offered to the user on request.

The features of the invention disclosed in the above descriptions, the claims and the drawing may be of importance both individually and in any combination for the implementation of the invention in its various embodiments.

The invention claimed is:

1. A method for the combined analysis of a sample with objects to be analyzed, in particular a sample with biological objects, comprising the steps of:
    obtaining measurement results for one or more of the objects to be analyzed in the sample, by analyzing the one or more objects to be analyzed by an imaging method of measurement,
    determining at least one first optical property of the one or more objects to be analyzed from the measurement results,
    obtaining probe-microscopic measurement results for the one or more objects to be analyzed, by analyzing the one or more objects to be analyzed by a probe-microscopic method of measurement,
    determining at least one first mechanical property of the one or more objects to be analyzed from the probe-microscopic measurement results, and
    assigning the at least one first optical property and the at least one first mechanical property to one another after optional prior intermediate processing and at least one of the following:
    1) deriving information on sample properties of the sample from the imaging measurement results, and subsequently taking and using the information on sample properties when carrying out the probe-microscopic method of measurement; and
    2) deriving information from the probe-microscopic measurement results and subsequently using the information obtained from said step of deriving information from the probe-measurement results when carrying out the imaging method of measurement.

2. The method according to claim 1, further comprising the steps of deriving positional information about the position of the one or more objects to be analyzed in the sample is derived, as information on sample properties, from the imaging measurement results and taking the positional information into account for positioning a measuring probe used in the probe-microscopic method of measurement relative to the sample.

3. The method according claim 1, further comprising the step of arranging the sample in a fluidic cell in the imaging and the probe-microscopic methods of measurement.

4. The method according to claim 1, further comprising the step of analyzing biological cells as objects to be analyzed in the sample in the imaging and the probe-microscopic methods of measurement.

5. The method according to claim 1, further comprising the step of obtaining further probe-microscopic measurement results for the one or more objects to be analyzed by analyzing the one or more objects to be analyzed again by the probe-microscopic method of measurement, using altered observation parameters, which differ from observation parameters of probe-microscopic methods of measurement that were carried out previously.

6. The method according to claim 1, further comprising the step of carrying out the imaging method of measurement using at least one measurement technique selected from the following group of measurement techniques: electrical imaging method of measurement such as patch-clamp and impedance measurement, chemical imaging technique such as local pH measurement or ion-selective value measurement and optical imaging method of measurement.

7. The method according to claim 1, further comprising the step of carrying out the probe-microscopic method of measurement using at least one measurement technique selected from the following group of measurement techniques: scanning probe microscopy, atomic force microscopy and optical force microscopy.

8. A device for carrying out combined analysis of a sample with objects to be analyzed, in particular a sample with biological objects, with:
   an imaging measuring device, which is configured for obtaining measurement results for one or more of the objects to be analyzed in the sample, by analyzing the one or more objects to be analyzed by an imaging method of measurement, and for determining at least one first optical property of the one or more objects to be analyzed from the measurement results,
   a probe-microscopic measuring device, which is configured for obtaining probe-microscopic measurement results for the one or more objects to be analyzed, by analyzing the one or more objects to be analyzed by a probe-microscopic method of measurement, and for determining at least one first mechanical property of the one or more objects to be analyzed from the probe-microscopic measurement results, and
   an evaluating device, which is coupled to the imaging measuring device and to the probe-microscopic measuring device and is configured for assigning the at least one first optical property and the at least one first mechanical property to one another, after optical prior intermediate processing; and
wherein the device for carrying out combined analysis of a sample with objects to be analyzed includes at least one of the following:
1) data from the imaging measuring device includes information on sample properties of the sample, and subsequently using the information on the sample properties when using the probe-microscopic measuring device; and
2) information derived from the probe-microscopic measurement results is subsequently used when using the imaging measuring device.

* * * * *